(12) United States Patent
Long et al.

(10) Patent No.: US 11,464,501 B2
(45) Date of Patent: Oct. 11, 2022

(54) BIOPSY DEVICE

(71) Applicant: National University of Ireland, Galway, Galway (IE)

(72) Inventors: Damien Long, Galway (IE); Edmund Brennan, Galway (IE); Eugene Skelton, Dublin (IE); Anthony Wright, Dublin (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 129 days.

(21) Appl. No.: 16/671,914

(22) Filed: Nov. 1, 2019

(65) Prior Publication Data

US 2020/0138420 A1    May 7, 2020

(30) Foreign Application Priority Data

Nov. 1, 2018    (EP) .................................... 18203974

(51) Int. Cl.
*A61B 10/02* (2006.01)
(52) U.S. Cl.
CPC .. *A61B 10/0275* (2013.01); *A61B 2010/0208* (2013.01)
(58) Field of Classification Search
CPC . A61B 10/0275; A61B 10/0233; A61B 10/02; A61B 2010/0208
See application file for complete search history.

(56) References Cited

U.S. PATENT DOCUMENTS 4,735,215 A    4/1988 Goto et al.
4,881,551 A    11/1989 Taylor
(Continued)

FOREIGN PATENT DOCUMENTS

DE    10050742 A1    4/2001
WO    2016049347 A1    3/2013

OTHER PUBLICATIONS

Extended European Search Report, European Application No. 18203974. 3, dated May 13, 2019, 9 pages.

*Primary Examiner* — Sean P Dougherty
(74) *Attorney, Agent, or Firm* — Husch Blackwell LLP

(57) ABSTRACT

A biopsy device comprising: a cannula comprising an elongate cannula body extending between a cannula distal end and a cannula proximal end to define a lumen, wherein the cannula comprises a cutting portion at the cannula distal end; a stylet comprising an elongate body having a stylet distal end and a stylet proximal end, the stylet being slidably disposed within the lumen, wherein the stylet comprises a tissue sampling portion. The tissue sampling portion is formed by a notch in the body of the stylet at or near the stylet distal end. The biopsy device further comprises an actuator assembly, the actuator assembly arranged to move the cannula relative to the stylet between a retracted position in which at least part of the tissue sampling portion is exposed and an extended position in which the cannula at least partly surrounds the tissue sampling portion. The actuator assembly comprises a cannula actuator moveable between a primed configuration and an actuated configuration to move the cannula between the retracted position and the extended position. The biopsy device further comprises a selective coupling mechanism arranged to provide a selective coupling between the actuator assembly and one or both of the stylet and the cannula.

15 Claims, 8 Drawing Sheets

(56) References Cited

U.S. PATENT DOCUMENTS

| | | | |
|---|---|---|---|
| 4,976,269 A | | 12/1990 | Mehl |
| 5,090,419 A | | 2/1992 | Palestrant |
| 5,161,542 A | | 11/1992 | Palestrant |
| 5,163,947 A | | 11/1992 | Kvalo et al. |
| 5,284,156 A | * | 2/1994 | Schramm ........... A61B 10/0275 600/567 |
| 5,316,013 A | | 5/1994 | Striebel et al. |
| 5,507,298 A | * | 4/1996 | Schramm ........... A61B 10/0275 600/567 |
| 5,535,755 A | * | 7/1996 | Heske ................ A61B 10/0275 600/567 |
| 5,538,010 A | * | 7/1996 | Darr .................. A61B 10/0275 600/567 |
| 6,273,861 B1 | * | 8/2001 | Bates ................. A61B 10/0275 600/567 |
| 2006/0089565 A1 | * | 4/2006 | Schramm ........... A61B 10/0275 600/568 |
| 2010/0121218 A1 | | 5/2010 | Mugan et al. |
| 2011/0152715 A1 | | 6/2011 | Delap et al. |
| 2012/0116248 A1 | | 5/2012 | McWeeney et al. |
| 2013/0030323 A1 | * | 1/2013 | Smith ................ A61B 10/0275 600/567 |
| 2013/0060161 A1 | | 3/2013 | Bacon |
| 2015/0238175 A1 | | 8/2015 | Seiger et al. |
| 2018/0008244 A1 | * | 1/2018 | Nishina .............. A61B 10/0275 |
| 2018/0098758 A1 | * | 4/2018 | Nishina ............... A61B 10/025 |

\* cited by examiner

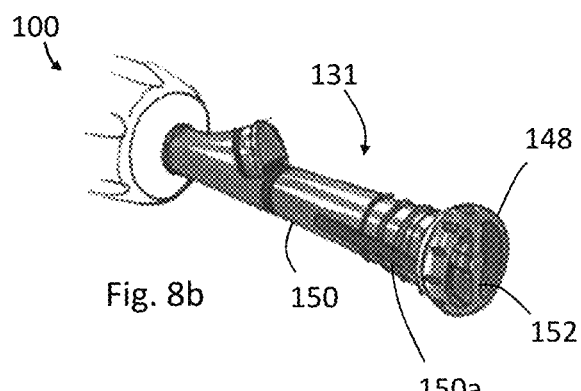
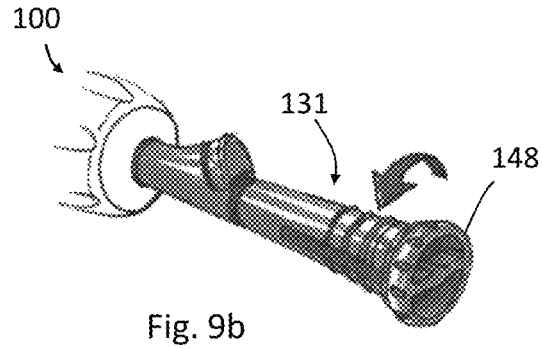
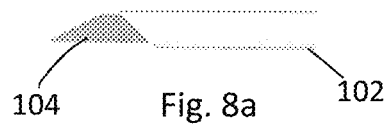
Fig. 8a
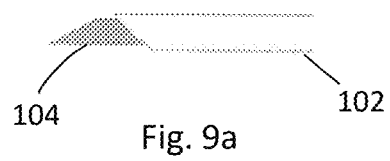
Fig. 9a
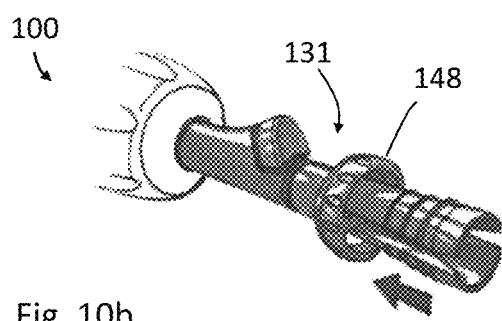
Fig. 10b
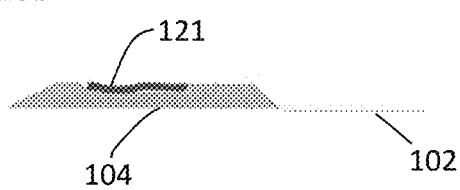
Fig. 10a

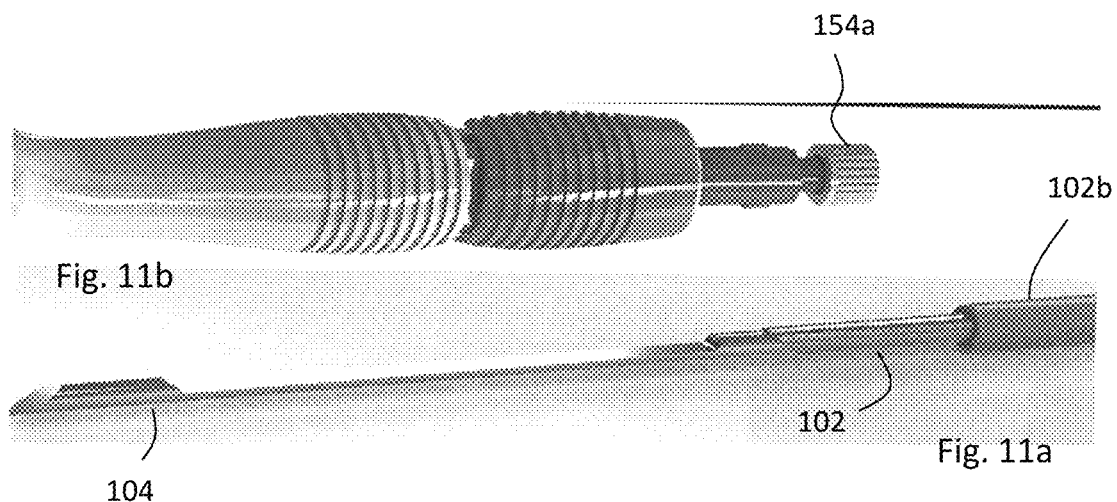
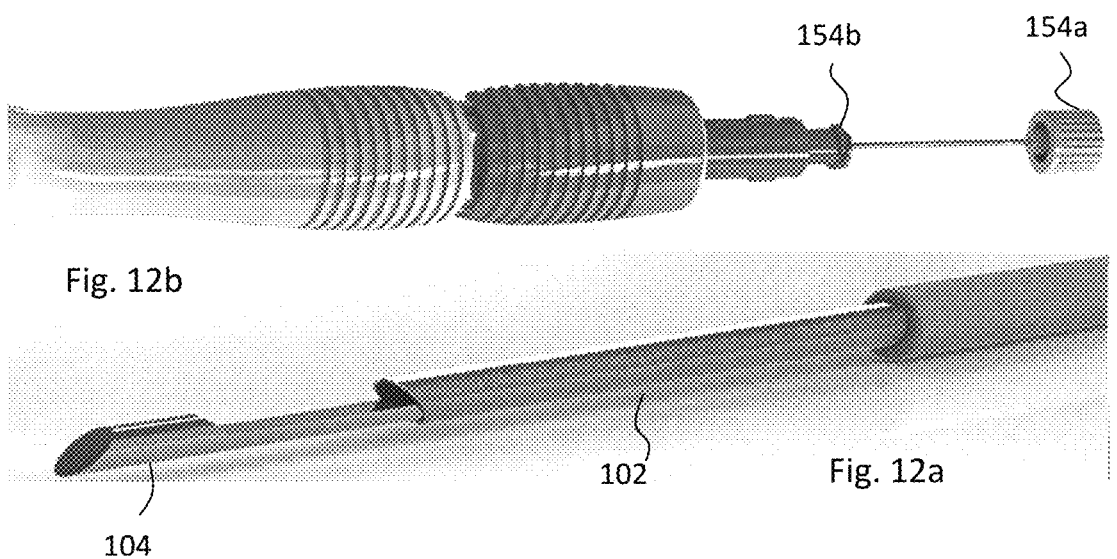
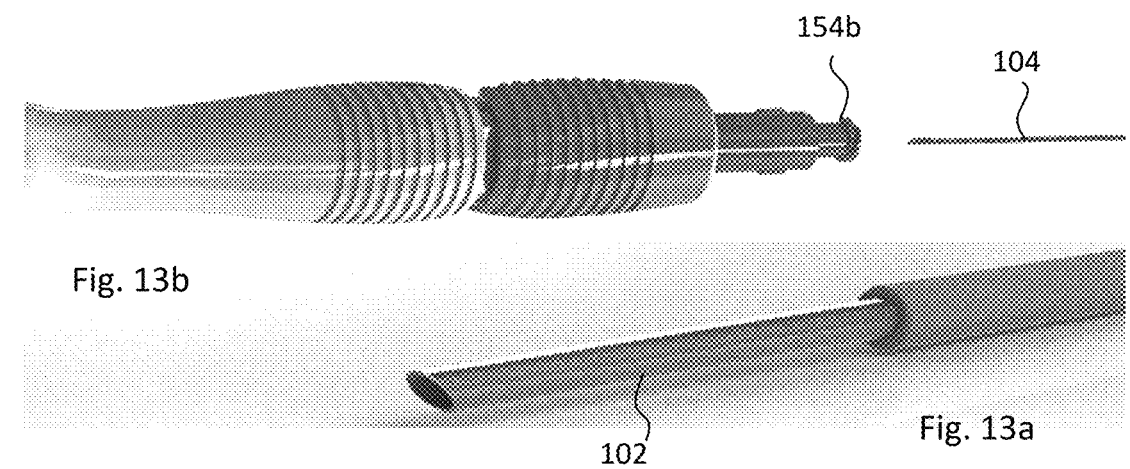

BIOPSY DEVICE

CROSS REFERENCE TO RELATED APPLICATIONS

This application claims priority to European Patent Application No. 18203974.3, filed Nov. 1, 2018, and is incorporated herein by reference in its entirety.

FIELD

The present application relates to a biopsy device. In particular, the present application relates to the field of biopsy devices that may be used to take a tissue sample from the body, for example percutaneously, transluminally, or endoscopically.

BACKGROUND

Biopsy devices are known that allow percutaneous acquisition of a high quality tissue core sample suitable for histological analysis using a two part biopsy needle. The biopsy needle has an inner part or stylet having a tissue collecting or specimen notch formed near a stylet distal end. An outer part or cannula has a point on a cannula distal end and encloses the stylet. The cannula and stylet are arranged so that the cannula point advances over the stylet in order to cover the specimen notch. In use, advancement of the stylet through tissue will first result in tissue prolapsing into the recessed notch. Subsequent forward movement of the cannula cuts out a specimen of the prolapsed tissue, so that the specimen becomes retained in the specimen notch of the stylet. The biopsy needle may then be withdrawn and the tissue sample recovered from the stylet. These devices may incorporate a spring-loaded actuator to advance the cannula over the stylet very quickly in order to prevent the prolapsed tissue in the specimen notch from being displaced as the cannula advances over the stylet.

Operation of a known biopsy device 1 is shown in FIGS. 1a to 1c. The biopsy device 1 has a cannula 2 and a stylet 4. FIG. 1a shows a starting position in which a spring loaded actuator 6 is in a relaxed state. The actuator 6 is coupled to the cannula 2 and stylet 4 such that withdrawal of the stylet drags the cannula with it which in turn compresses the spring. FIG. 1b shows the actuator 6 in a primed configuration and the stylet 4 withdrawn. The stylet can then be advanced relative to the cannula 2 so as to expose the sample collection tray 8 near its distal end. The stylet 4 can be advanced up to a set end-stop corresponding to the tray 8 being fully exposed outside of the cutting cannula 2, as shown in FIG. 2c. The actuator 8 is then activated, typically by advancing the stylet 4 beyond the predetermined end-stop. This movement releases a latch for the spring so that it is released from its compressed state to drive the cannula 2 distally to cut tissue. Once the actuator 8 has been activated in this way the biopsy device returns to its original starting configuration. By coupling the stylet 4 and cannula 2 to the actuator in this way the biopsy device may be more easily operated. Coupling of the stylet and cannula to the actuator provides operating benefits. For example, withdrawal of the stylet results in corresponding withdrawal of the cannula, while advancement of the stylet up to the set end-stop can be performed without any advancement of the cannula.

There are a number of drawbacks with a biopsy device such as this. In order to recover the tissue sample from the tray, the stylet must be advanced out of the cannula to expose the tray holding the specimen. This must be done by first moving the biopsy device to the state shown in FIG. 1b and then advancing the stylet out of the cannula as shown in FIG. 1c. In this configuration, the actuator has been primed ready for release. This may increase actual or perceived risk of a needle-stick injury caused by inadvertent activation of the actuator.

A further drawback is that it is difficult to facilitate aspirated collection of tissue from the biopsy area using the known biopsy device. Because the stylet component usually fills the through-lumen of the cannula, it is not possible to provide suction/aspiration through the cannula lumen. The coupling between the stylet and the actuator mean that the stylet cannot be removed from the device. Although a tissue biopsy device generally provides greater utility, there are instances where the ability to switch between aspirated tissue collection via the cannula lumen and core tissue collection via the stylet tray is desirable.

Another drawback may become apparent when the known biopsy device is used in conjunction with an endoscope or other flexible intraluminal device. In this case, an additional protective outer sheath may be provided. The stylet and cannula distal tip are withdrawn into the protective sheath prior to insertion of the biopsy device into an endoscope working channel. As the biopsy device tip is sheathed it is prevented from directly contacting or damaging the endoscope working channel during insertion.

In the relaxed position of the actuator described above (i.e. the starting position shown in FIG. 1a) the tip of the stylet and cannula may reside just inside the distal end of the sheath. When priming the actuator however, the stylet and cannula are retracted further inside the protective sheath (i.e. both the stylet and the cannula are moved proximally when moving to the primed configuration shown in FIG. 1b). This presents a risk that the stylet may pierce though the protective sheath when the user attempts to manoeuvre the stylet/cannula assembly out of the sheath in preparation to puncture tissue at the biopsy site. To mitigate this risk, the user may attempt to manually readjust the position of the biopsy device so that the stylet and cannula tip are correctly aligned with the distal end of the protective sheath. This however 1) consumes a valuable amount of the device's available travel and 2) presents an opportunity for this readjustment step to be inadvertently overlooked by the user or not performed correctly, potentially causing serious damage to the working channel of the endoscope.

An improved biopsy device is therefore required to address some or all of these drawbacks.

SUMMARY

In a first aspect, the present application provides: a biopsy device, comprising any one or more of the following features: a cannula comprising an elongate cannula body extending between a cannula distal end and a cannula proximal end to define a lumen, wherein the cannula comprises a cutting portion at the cannula distal end; a stylet comprising an elongate body having a stylet distal end and a stylet proximal end, the stylet being slidably disposed within the lumen, wherein the stylet may comprise a tissue sampling portion, the tissue sampling portion may be formed by a notch in the body of the stylet at or near the stylet distal end; an actuator assembly, the actuator assembly arranged to move the cannula relative to the stylet between a retracted position in which at least part of the tissue sampling portion is exposed and an extended position in which the cannula at least partly surrounds the tissue sampling portion, the actuator assembly comprising a cannula actuator moveable between a primed configuration and an actuated configuration to move the cannula between the retracted position and the extended position; and a selective coupling mechanism arranged to provide a selective coupling between the actuator assembly and one or both of the stylet and the cannula.

By providing a selective coupling mechanism, the biopsy device allows the user to switch between a coupled configuration in which the cannula and/or the stylet are operatively coupled to the actuator assembly, and an uncoupled configuration in which there is no such operative coupling so that they can be manipulated without affecting the actuator assembly. This allows free movement of the cannula and/or stylet in one mode of operation; and control of the actuator assembly to be linked to movement of the stylet, and/or control of the cannula by the actuator assembly, in another mode of operation.

This may allow the user to move the stylet freely without any effect on the actuator when desired. For example, the stylet may be moved to an extended position to retrieve the sample in the uncoupled configuration, whereas in the coupled configuration such movement would cause operation of the actuator assembly (e.g., moving it to the primed configuration or releasing it from the primed configuration). Decoupling the actuator assembly may also allow the user to remove the stylet from the cannula completely to allow aspiration through the lumen of the catheter. Decoupling the cannula from the actuator assembly may allow the user to freely reposition the distal tip of the cannula relative to a protective sheath surrounding the cannula and stylet.

Optionally, the selective coupling mechanism may comprise a stylet coupler, the stylet coupler being movable between: a stylet coupled configuration in which the stylet is coupled to the actuator assembly; and a stylet uncoupled configuration in which the stylet is uncoupled from the actuator assembly. This may allow the stylet to be decoupled from the actuator assembly so that it can be moved freely when desired.

Optionally, the actuator assembly comprises a stylet actuator configured to actuate movement of the stylet relative to the cannula. The stylet actuator may be further configured to control or cause movement of the cannula actuator between the actuated configuration and the primed configuration. This allows cannula actuator to be controlled by the stylet actuator to facilitate ease of use.

Optionally, the stylet actuator and the cannula actuator may be operably coupled in the stylet coupled configuration such that operation of the stylet actuator to cause movement of the stylet in a distal direction relative to the cannula activates movement of the cannula actuator from the primed configuration to the actuated configuration. This may allow the user to control the cannula actuator using the same action used to position the stylet. This may facilitate ease of use.

Optionally, the actuator assembly may comprise a locking mechanism arranged to releasably lock the cannula actuator in the primed configuration. The locking mechanism may be releasable by the stylet actuator. This may allow the user to activate the cannula actuator in the same action as moving the stylet via the stylet actuator.

Optionally, the stylet actuator and the cannula actuator may be operably coupled in the stylet coupled configuration such that operation of the stylet actuator causes movement of the stylet relative to the cannula, which causes movement of the cannula actuator from the actuated configuration to the primed configuration. This may allow the user to prime the cannula actuator using the same action as that causing movement of the stylet via the stylet actuator. This may help to facilitate ease of use.

Optionally, in the stylet uncoupled configuration, the stylet may be movable in a proximal direction relative to the cannula so that it can be removed from the lumen of the cannula. This may allow the stylet to be removed from the cannula lumen to allow access to the tissue sampling portion or to allow suction to be applied through the cannula lumen.

Optionally, the stylet coupler may comprise a luer lock connector in communication with the lumen of the cannula and a corresponding luer lock connector provided on the stylet. The luer lock connector in communication with the cannula lumen may be adapted to provide a connection to another device having a corresponding luer lock connector when the stylet is removed from the lumen of the cannula. This may allow another device to be attached to the cannula via the luer connector once the stylet has been removed from the cannula lumen.

Optionally, a rotation of at least part of the stylet coupler may cause movement of the stylet coupler between the stylet coupled configuration and the stylet uncoupled configuration. This may allow convenient switching between a coupled and uncoupled mode of operation to facilitate ease of use.

Optionally, the stylet coupler may comprise a release wheel mounted to the stylet, the release wheel having an engagement member, and a slotted member coupled to the actuator assembly. The slotted member may be adapted to receive the engagement member. In the stylet uncoupled configuration, the engagement member may be aligned with a slot of the slotted member such that the stylet can move freely relative to the actuator assembly. In the stylet coupled configuration, the release wheel may be rotated such that the engagement member is misaligned with the slot, whereby the engagement member abuts the slotted member such that the actuator assembly is operably coupled to the stylet. This may provide a mechanism to switch between the coupled and uncoupled configuration that is quick and easy to operate.

Optionally, the selective coupling mechanism may comprise a cannula coupler, the cannula coupler being movable between: a cannula coupled configuration in which the cannula is coupled to the actuator assembly; and a cannula uncoupled configuration in which the cannula is uncoupled from the actuator assembly. This may allow the cannula to be decoupled from the actuator assembly so that it can be moved freely when desired.

Optionally, in the cannula coupled configuration the cannula is coupled to the actuator assembly such that movement between the primed and actuated configurations of the cannula actuator causes movement of the cannula; and in the cannula uncoupled configuration the cannula can be moved freely relative to the cannula actuator. This allows the cannula to be repositioned independently of the cannula actuator.

Optionally, a rotation of at least part of the cannula coupler may cause movement of the cannula coupler between the cannula coupled configuration and the cannula uncoupled configuration. This may allow convenient switching between a coupled and uncoupled mode of operation to facilitate ease of use.

Optionally, one of the cannula actuator and the cannula coupler may comprise a slotted member and the other of the cannula actuator and cannula coupler may comprise a corresponding engagement member. In the cannula uncoupled configuration, the engagement member may be aligned with a slot of the slotted member such that the cannula can move freely relative to the actuator; and in the cannula coupled configuration, the cannula coupler is rotated such that the engagement member is misaligned with the slot whereby the engaging member engages the slotted member and movement of the cannula actuator causes movement of the cannula. This may provide a mechanism to switch between the coupled and uncoupled configuration that is quick and easy to operate.

The cannula actuator may comprise a biasing member formed from a resilient member. In the primed configuration, the cannula actuator may be biased towards the actuated configuration. This may allow the cannula actuator to rapidly move the cannula over the stylet to cleanly cut tissue. The resilient member may be a coiled spring.

In another aspect, the present application provides a method of collecting a tissue sample using the biopsy device of the first aspect, the method comprising: moving the cannula actuator from the actuated configuration to the primed configuration; extending the stylet relative to the cannula to expose the tissue sampling portion and to receive tissue in the tissue sampling portion; moving the cannula actuator from the primed configuration to the actuated configuration to cause movement of the cannula relative to the stylet, whereby tissue in the tissue sampling portion is cut from the surrounding tissue so that a tissue sample is taken, wherein the method further comprises using the selective coupling mechanism to decouple the stylet and/or the cannula from the actuator assembly.

Optionally, the method may comprise: using the selective coupling mechanism to decouple the stylet from the actuator assembly once the cannula actuator is moved to the actuated configuration and a tissue sample taken; and moving the stylet independently of the cannula actuator to recover the tissue sample.

Optionally, once the selective coupling mechanism has been decoupled, the stylet may be moved in a distal direction to expose the tissue sampling portion and a tissue sample recovered. Alternatively, the stylet may be moved in a proximal direction so that it can be removed completely from the cannula lumen to recover the tissue sample.

Optionally, the method may comprise: while the selective coupling mechanism is in an uncoupled configuration in which the cannula is uncoupled from the actuator assembly and the cannula actuator has been moved to the primed configuration, moving the cannula independently of the cannula actuator to reposition its distal end; and once repositioned, using the selective coupling mechanism to couple the cannula and the actuator assembly. The distal end of the cannula may be aligned relative to a protective sheath surrounding the cannula.

Embodiments of the invention will now be described, by way of example only, with reference to the accompanying drawings, in which:

BRIEF DESCRIPTION OF THE DRAWINGS

FIGS. 1a to 1e show the operation of a prior art biopsy device;

FIG. 2b shows a side sectional schematic view of a proximal end of the biopsy device shown in FIG. 2a;

FIGS. 3a to 7b show an operation sequence of the biopsy device of FIGS. 2a and 2b, where FIGS. 3a, 4a, 5a, 6a and 7a show the distal end of the biopsy device and FIGS. 3b, 4b, 5b, 6b and 7b show the corresponding proximal end;

FIGS. 8a to 10b show an embodiment of a stylet coupler of a biopsy device, where FIGS. 8a, 9a and 10a show a distal end of the biopsy device and FIGS. 8b, 9b and 10b show the corresponding proximal end;

FIGS. 11a to 13b show another embodiment of an stylet coupler of a biopsy device, where FIGS. 11a, 12a and 13a show a distal end of the biopsy device with FIGS. 11b, 12b and 13b showing the corresponding proximal end;

DETAILED DESCRIPTION

The present application relates to a biopsy device 100 for taking a tissue sample from the human or animal body. The biopsy device may be used with any suitable method of delivering a biopsy device to a site of interest where a tissue sample is to be taken. For example, the biopsy device may be suitable for endoscopic, transluminal or percutaneous use, or may be used with other methods of delivery as would be apparent to a person skilled in the field of the invention.

Figure 1A:
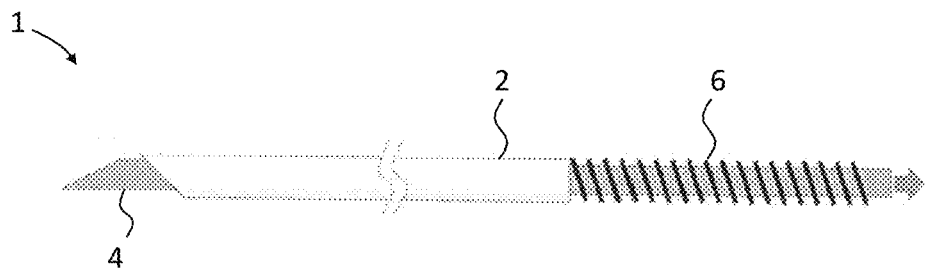
Figure 1B:
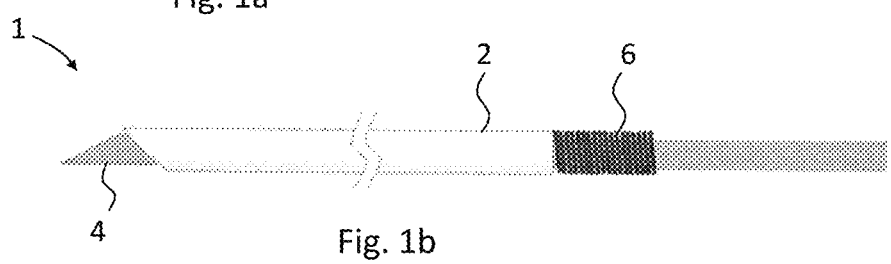
Figure 1C:
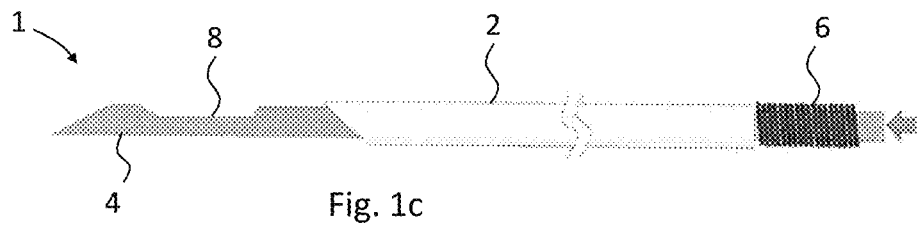
Figure 1D:
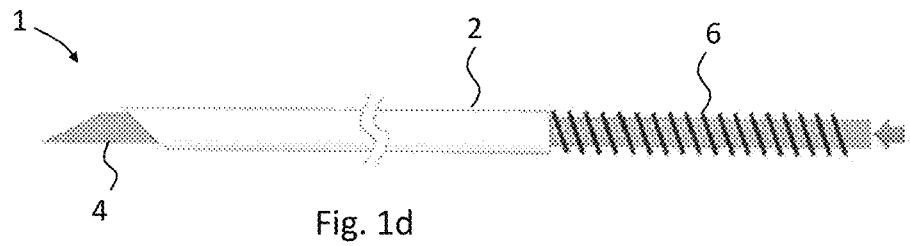
Figure 2A:
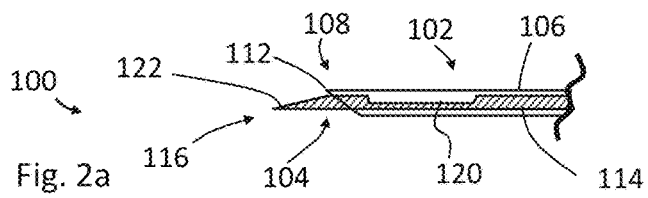
FIG. 2a shows a sectional schematic view of a distal end of a biopsy device according to an embodiment.
Figure 2B:
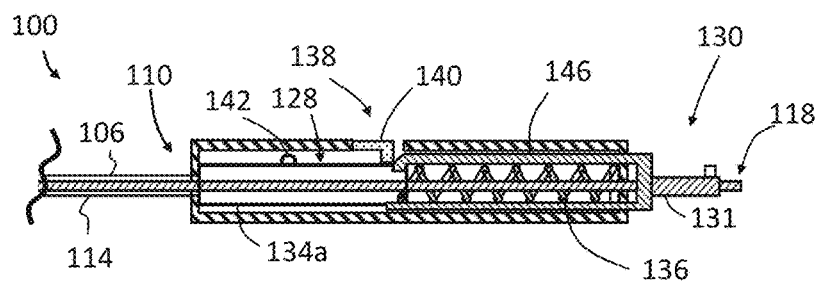
Figure 2C:
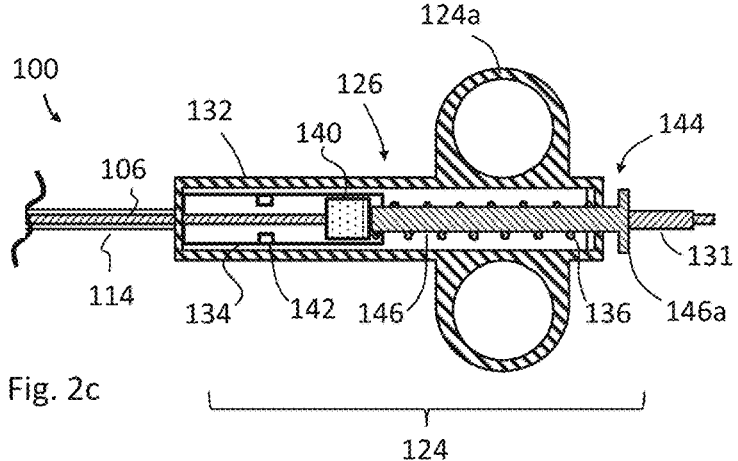
FIG. 2c shows a top sectional schematic view of the proximal end of the biopsy device shown in FIG. 2b.
Figure 3A:
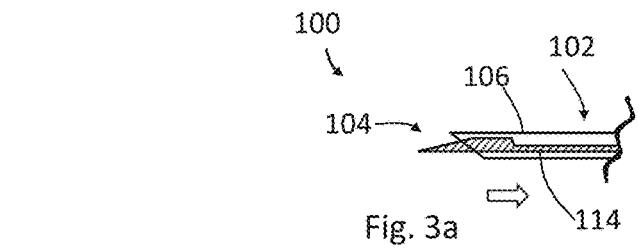
Figure 3B:
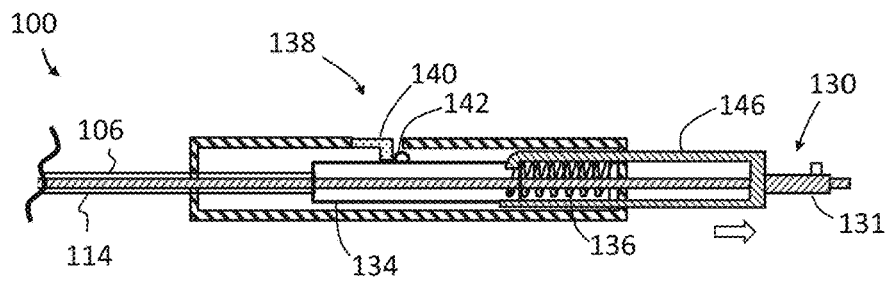

An embodiment of the biopsy device 100 is shown schematically in FIGS. 2a, 2b and 2c. FIG. 2a shows a cross section of a distal end of the biopsy device, with a cross section of a proximal end shown in FIGS. 2b and 2c as a side and top view respectively. Not all of the length of the biopsy device connecting the distal and proximal ends is shown in FIGS. 2a, 2b, and 2c to aid clarity.

The biopsy device 100 generally comprises a cannula 102 and a stylet 104. The cannula 102 comprises an elongate cannula body 106, which extends between a cannula distal end 108 (the end nearest to the patient or biopsy site in use) and a cannula proximal end 110 (the end nearest to the operator/device handle). The elongate cannula body 106 defines a lumen or hollow tube extending from the cannula distal end 108 to the cannula proximal end 110. The cannula 102 further comprises a cutting portion 112 located at (or near) the cannula distal end 108. The cutting portion 112 may comprise one or more cutting edges adapted to cut tissue during use of the biopsy device 100 to obtain a sample.

In the described embodiment, the cutting portion 112 comprises a cutting edge extending around the circumference of the distal end of the cannula. In other embodiments, the cutting portion 112 may comprise a cutting edge extending around only part of the circumference of the cannula 102. The cutting portion 112 may comprise a tissue piercing portion adapted to pierce tissue at the biopsy site. The tissue piercing portion may comprise a point or protrusion of the cutting edge at a position around the circumference of the cannula distal end 108. In other embodiments, the tissue piercing portion may be formed by a needle tip or point. The tissue piercing portion is adapted to make first contact with the tissue during cutting to provide effective insertion into the tissue.

The stylet 104 comprises an elongate stylet body 114 having a stylet distal end 116 and a stylet proximal end 118. The stylet 104 is slidably disposed within the lumen of the cannula such that it may slide along its length relative to the cannula 102. The stylet 104 further comprises a tissue sampling portion 120 adapted to receive a sample of tissue cut by the cannula cutting portion 112. The tissue sampling portion 120 may comprise a notch or slot in the body of the stylet 104 defining a cavity or recess extending along its length in which tissue may be received. The tissue sampling portion 120 may be located at or near to the stylet distal end 116 of the stylet 104 as shown in FIG. 2a. In other words, the tissue sampling portion 120 may be located in a distal region of the stylet 104, and may not necessarily be at the very distal tip. Other shapes and types of notch that may receive tissue are possible with the shape shown in FIG. 2a being only one example.

In the described embodiment, the stylet 104 further comprises a stylet cutting portion 122 to aid insertion of the stylet 104 into tissue during use of the biopsy device 100. The stylet cutting portion 122 may be formed from a tapered portion of the elongate stylet body 114 at the stylet distal end 116. The cannula distal end 108 may be proximal of the stylet cutting portion 122 in an extended configuration of the cannula 102 as will be described later. In other embodiments, the stylet cutting portion 122 may be any other suitable shape to aid insertion of the stylet 104 into tissue during use. In yet other embodiments, the stylet cutting portion 122 may be absent.

In the described embodiment, the cannula 102 and stylet 104 are generally circular in cross section. In such an embodiment, both the elongate cannula body 106 and the elongate stylet body 114 may have a generally circular cross section. The lumen may also have a generally circular cross section to accommodate the elongate stylet body 114. In other embodiments, the elongate cannula body 106 may have any other suitable cross section, and may, for example, be elliptical or square. In other embodiments, elongate stylet body 114 and the lumen may also have any other suitable cross section shape. In the described embodiment, the cross section of the elongate stylet body 114 and the elongate cannula body 106 is generally constant along their length. In yet other embodiments, the cross section may vary along the length of either the elongate cannula body 106 and/or the elongate stylet body 114 or the lumen. In the described embodiment, the lumen is formed such that it is concentric with the elongate cannula body 106 such that the elongate cannula body 106 has a constant thickness. In yet other embodiments, the lumen may be off-centre relative to a central axis of the cannula body i.e. the thickness of the elongate cannula body 106 may vary around its circumference. In some embodiments, the outer cross section of the cannula 102 may be a different shape to that of the lumen.

In some embodiments, the cannula 102 and the stylet 104 may be made from metal such as stainless steel. In other embodiments, either the cannula 102, the stylet 104, or both may be made from any other suitable material such as cobalt-chromium alloys, Nitinol, or a combination thereof. In some embodiments, the combined stylet 104 and cannula 102 may be substantially rigid and inflexible. Such an embodiment may be suited to percutaneous or other straight-line use where significant bending of the biopsy device 100 is not required to reach the biopsy site. In other embodiments, the combined stylet 104 and cannula 102 may be substantially flexible. In such an embodiment, the biopsy device 100 is suited to pass through the working channel of an endoscope or the like. This may allow access to biopsy sites that are within the body and require bending of the biopsy device 100 to reach them. In some embodiments, the biopsy device 100 may further comprise an outer member surrounding the cannula body 106 along at least part of its length. The cannula may be arranged to slide relative to the outer member during use as will be described later. The outer member may, for example, form a protective sheath adapted to protect the inner wall of an endoscope working channel when the biopsy device 100 is passed along its length. In such an embodiment, the sheath may be made from a deformable material such as a polymer or the like to protect the endoscope or the user when handling the biopsy device.

One or both of the elongate cannula body 106 and the elongate stylet body 114 may be formed at least partly from a flexible material. In some embodiments, in order to improve the flexibility of the biopsy device 100, the cannula 102 may comprise one or more flexible portions along at least part of the length of the elongate cannula body 106. The flexible portions may comprise a weakened portion (or portions) of the elongate cannula body 106 such as a spiral cut slotted section or a torque tube section. In some embodiments, the stylet 104 may also comprise similar flexible portion(s) to improve its flexibility. In other embodiments, the cannula 102 or the stylet 104 may have a sufficient degree of flexibility due to their material of construction and physical size without the need for additional flexible portions.

The biopsy device 100 further comprises a handle portion 124 disposed at or near the proximal end of the device. At least one of the stylet 104 and the cannula 102 may be movable in a distal or proximal direction along their length relative to the handle portion 124 so that they may be moved relative to each other in order to trap a tissue sample in the tissue sampling portion 120. The handle portion 124 may comprise a suitable gripping structure such as one or more finger loops 124a with which the user may grip and manipulate the biopsy device 100 during use.

Figure 4A:
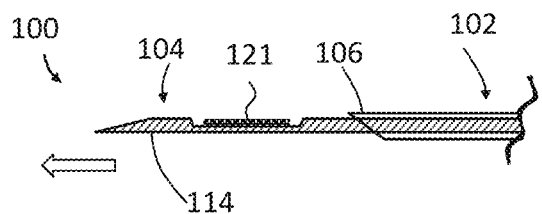
Figure 4B:
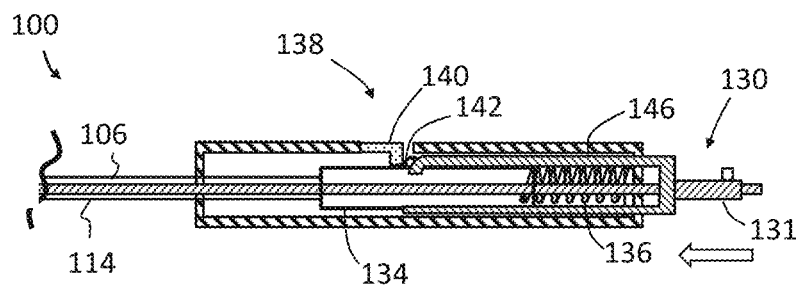

The biopsy device 100 further comprises an actuator assembly 126 mounted in the handle portion 124. The actuator assembly 126 is arranged to move the cannula 102 relative to the stylet 104 between a retracted position (as illustrated in FIG. 4a) in which at least part of the tissue sampling portion 120 is exposed and an extended position (as illustrated in FIG. 2a) in which the cannula 102 at least partly surrounds the tissue sampling portion 120. When in the extended position the distal end 116 of the stylet 104 may still protrude from the distal end 108 of the cannula 102 so that the cutting portion 122 of the stylet 104 protrudes from the distal end 108 of the cannula 102. This may allow tissue to be pierced during use. In other embodiments, when in the extended position, the cannula 102 may completely surround or encapsulate the stylet 104 such that the stylet does not protrude from its distal end 108.

The actuator assembly 126 comprises a cannula actuator 128 that is moveable between a primed configuration and an actuated configuration to move the cannula 102 between the retracted position and the extended position. When released or actuated from the primed configuration, the cannula 102 may be moved by the cannula actuator 128 to cut tissue that has prolapsed into the tissue sampling portion 120. The actuator assembly 126 may provide a rapid movement of the cannula 102 relative to the stylet 104 to help cleanly cut tissue (e.g. using a spring loaded cannula actuator). In other embodiments, a slower more controlled actuation of the cannula 102 may be provided using other types of the cannula actuator 128.

The biopsy device 100 further comprises a selective coupling mechanism 130 arranged to provide a selective coupling between the actuator assembly 126 and one or both of the stylet 104 and the cannula 102. This may provide the biopsy device with a mode of operation in which the cannula 102 and/or the stylet 104 can be decoupled from the actuator assembly 126 so that they can be moved independently of it. This may allow repositioning of the cannula 102 or stylet 104 (e.g. relative to an outer sheath of the biopsy device), or access to the tissue sampling portion 120, without any operation of the actuator assembly 126.

FIGS. 2a, 2b, and 2c illustrate an embodiment in which the selective coupling mechanism 130 comprises a stylet coupler 131 arranged to selectively couple the stylet 104 and the actuator assembly 126.

The stylet coupler 131 may be movable between a stylet coupled configuration in which the stylet 104 is operably coupled to the actuator assembly 126, and a stylet 104 uncoupled configuration in which the stylet 104 is operably uncoupled from the actuator assembly 126. In the coupled configuration, the stylet 104 is coupled to part of the actuator assembly 126, whereas in the uncoupled configuration there is no coupling between them so that the stylet 104 can be moved freely and independently of the actuator assembly 126. This may allow movement of the stylet 104 and cannula 102 to be linked together in the coupled configuration (e.g. operation of the cannula actuator to move it from the actuated to the primed configuration, or vice versa, may correspond to an associated movement of the stylet). In the uncoupled configuration, the stylet 104 may be moved freely when required without any resulting effect on the actuator assembly 126 or the position of the cannula 102.

In the stylet uncoupled configuration, the stylet 104 may therefore be movable in a distal direction relative to the cannula 102 to an extended position in which a portion of the stylet 102 having the tissue sampling portion 120 is extended past the distal end 108 of the cannula 102. This may facilitate access to the collected tissue without having to set the actuator into its primed configuration. In the stylet uncoupled configuration, the stylet 104 may additionally or alternatively be movable in a proximal direction relative to the cannula 102 so that it can be removed from the lumen of the cannula 102. This may again facilitate access to the collected tissue, and allow aspiration to be applied to the cannula lumen. Both of these actions may be carried out without any use of or effect on the actuator assembly.

In the embodiment illustrated in FIGS. 2a, 2b, and 2c, the actuator assembly 126 comprises a housing 132 forming part of the handle portion 124 at the distal end of the biopsy device 100. The cannula 102 may be fixedly mounted to the cannula actuator 128 which comprises a carriage in the form of a sliding member 134 arranged to slide within the housing 132 to provided relative movement of the cannula 102 relative to the housing 132 (and the handle portion 124 of the biopsy device 100).

The cannula actuator 128 may comprise a biasing member 136 formed from a resilient member. The biasing member 136 may be coupled between the sliding member 134 and the housing 132 to provide relative movement between them. The resilient member may be a coiled spring as illustrated in the figures. Other resilient members may be used, such as other forms of a spring. In the primed configuration, the cannula actuator 128 may be biased towards the actuated configuration by the action of the biasing member 136. When released from the primed configuration, the cannula actuator 128 may move the cannula 102 rapidly from the retracted to extended position to cut tissue and trap a tissue sample within the tissue sampling portion 120 of the stylet 104.

In other embodiments, other forms of a cannula actuator may be provided to move the cannula 102 relative to the housing 132 and so relative to the stylet 104. For example, an electric actuator, pneumatic, or hydraulic actuator may be provided to form the cannula actuator.

The actuator assembly 126 may further comprise a locking mechanism 138 arranged to releasably lock the cannula actuator 128 in the primed configuration. When the locking mechanism 138 is released, the cannula actuator 128 may move from the primed configuration to the actuated configuration by the action of the biasing member 136. In the described embodiment, the locking mechanism 138 comprises a catch 140 disposed in a wall of the housing 132. The catch 140 may engage with a protrusion 142 on the sliding member 134 to restrict its movement within the housing 132.

The catch 140 is only one example of a locking mechanism 138 that may be used to lock the movement of the cannula actuator 128 against the action of the biasing member 136 in the primed configuration. Other forms of locking mechanism may be provided, such as a latch, a locking pin, or snap-fit coupling.

The actuator assembly 126 may further comprise a stylet actuator 144 configured to actuate movement of the stylet 104 relative to the cannula 102. The stylet actuator 144 may be configured to provide sliding movement of the stylet 104 relative to the housing 132 of the actuator assembly 126 and the handle portion 124 of the biopsy device 100. This may allow the stylet 104 to be advanced into tissue to collect a sample, and to allow the stylet 104 to be extended or retracted from the cannula lumen to recover the tissue sample 121.

The stylet actuator 144 may be further configured to control or cause the cannula actuator 128 to move between the actuated and primed configurations. It may, for example, allow the cannula actuator 128 to be moved from the actuated to the primed configurations, or may release it from the primed configuration to trigger actuation of the cannula movement. The stylet 104 may be releasably coupled to the stylet actuator 144 by the stylet coupler 131 so that the stylet 104 is releasably coupled to the actuator assembly 126. This allows the control of the stylet 104 position and the cannula actuator 128 to be linked when desired (e.g. when collecting a tissue sample), whilst also allowing the stylet 104 to be decoupled from the cannula actuator 128 to allow the stylet 104 to be independently moved (e.g. to access the tissue sampling portion 120) when desired.

The stylet actuator 144 may comprise a sliding member 146 which is slidably mounted within the housing 132 of the actuator assembly 126. The sliding member 146 may comprise a handle portion 146a with which it may be gripped during use. In this embodiment, the stylet actuator 144 is therefore manually operated to move the stylet 104. In other embodiments, the stylet actuator may comprise a biasing member to move the stylet 104 or other actuator device such as an electronic, pneumatic or hydraulic actuator may be used.

The stylet actuator 144 may be configured to engage with the cannula actuator 128 to cause movement from the actuated configuration to the primed configuration. The stylet actuator 144 and the cannula actuator 128 may be operably coupled in the stylet coupled configuration such that operation of the stylet actuator 128 to cause movement of the stylet 104 (e.g. in a proximal direction relative to the cannula) causes movement of the cannula actuator 128 from the actuated configuration to the primed configuration. As can be seen in FIGS. 2b and 2c, the sliding member 146 of the stylet actuator 144 may engage with the sliding member 134 of the cannula actuator 128 to which the cannula 102 is mounted. Movement of the stylet actuator 144 sliding member 146 relative to the housing 132 may cause a corresponding movement of the cannula actuator 128 sliding member 134 with respect to the housing 132 against the action of the biasing member 136. The stylet actuator 144 sliding member 146 may engage with the cannula actuator 128 so movement of the stylet actuator 144 in a proximal direction pulls the sliding member 134 so that it slides proximally within the housing 132. This allows the cannula actuator 128 to be moved to the primed configuration. If the stylet actuator 144 is also coupled to the stylet 104 by the stylet coupler 131, a corresponding proximal movement of the stylet 104 (relative to the housing 132) will also be produced.

In other embodiments, the cannula actuator 128 may be moved from the actuated to the primed configuration by a separate mechanism rather than the stylet actuator 144. The sliding member 134 of the cannula actuator 128 may, for example, be pulled directly in a proximal direction by any other suitable dedicated mechanism to which it is coupled.

The stylet actuator 144 may additionally or alternatively be configured to engage with the cannula actuator 128 to cause or activate movement between the primed configuration and the actuated configuration. The stylet actuator 144 and the cannula actuator 128 may be operably coupled in the stylet coupled configuration such that operation of the stylet actuator 144 to cause movement of the stylet 104 (e.g. in a distal direction) relative to the cannula activates movement of the cannula actuator 128 from the primed configuration to the actuated configuration. Part of the stylet actuator 144 may be configured to engage with the cannula actuator 128 to release the locking mechanism 138 so that the cannula actuator 128 may move from the primed configuration to the actuated configuration. As can be seen in FIGS. 2b and 2c, the sliding member 146 of the stylet actuator 144 may engage with the catch 140 to release it from engagement with the protrusion 142 on the sliding member 134 of the cannula actuator 128. Other types of engagement may be provided for different forms of locking mechanism and cannula actuator.

A distance of free travel of the stylet actuator 144 may be provided between its engagement with the sliding member 134 (to move it to the primed configuration) and engagement with the locking mechanism 138 (to release it from the primed configuration). This may allow the stylet 104 to be moved relative to the cannula 102 so that the distal end 116 of the stylet 104, including the tissue sampling portion 120, is extended past the distal end 108 of the cannula 102 to allow tissue to be received in the tissue sampling portion 120.

In yet other embodiments, the stylet actuator 144 may not be used to control the activation of the cannula actuator 128. The stylet actuator 144 may be used only to position the stylet 104, with separate mechanisms provided to move the cannula actuator 128 from the actuated to the primed configuration, and/or to release the locking mechanism 138.

Use of the biopsy device 100 illustrated in FIGS. 2a, 2b, and 2c to collect a tissue sample is shown in the sequence of FIGS. 3a to 7b. FIGS. 2a and 2b show a starting position in which the cannula actuator 128 is in the actuated configuration and the cannula 102 surrounds the tissue sampling portion 120.

A method of collecting a tissue sample may begin by moving the cannula actuator 128 from the actuated configuration to the primed configuration. This may be achieved by moving the sliding member 146 of the stylet actuator 144 in a proximal direction to store energy in the biasing member 136 (i.e. to compress the coiled spring). Movement of the stylet actuator 144 causes movement of the cannula actuator sliding member 134 (and also the cannula 102) along with the stylet 104 as the stylet coupler 131 is in the stylet coupled configuration. Once in the primed configuration, the locking mechanism 138 locks the cannula actuator 128 against movement back to the actuated position. The biopsy device 100 is then in the configuration shown in FIGS. 3a and 3b.

The method proceeds with extending the stylet 104 relative to the cannula 102 to expose the tissue sampling portion and receive tissue 121 in the tissue sampling portion 120. Movement of the stylet 104 is achieved by use of the stylet actuator 144. The sliding member 146 of the stylet actuator 144 is moved in a distal direction to extend the stylet 104. The biopsy device 100 is then in the configuration shown in FIGS. 4a and 4b. The stylet actuator 144 is moved within its range of free movement in which there is no engagement with the cannula actuator 128 as described above so that there is no associated movement of the cannula 102.

Figure 5A:
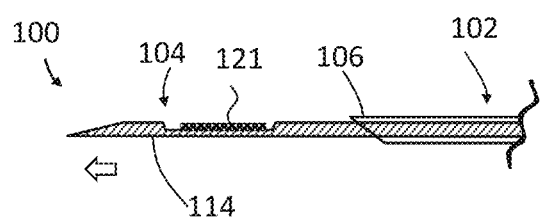
Figure 5B:
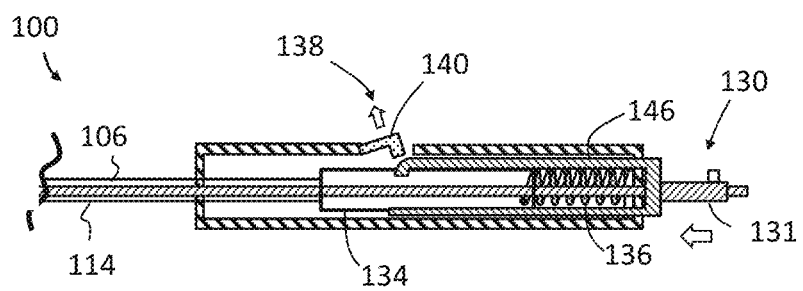
Figure 6A:
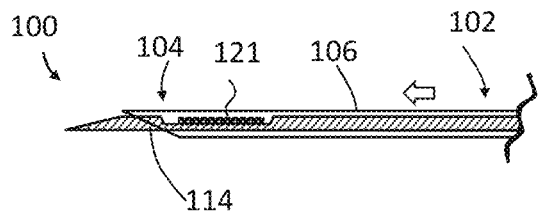
Figure 6B:
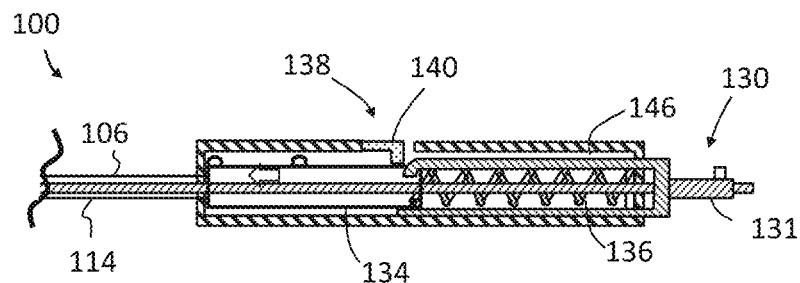

Once tissue is received in the tissue sampling portion 120, the method proceeds by moving the cannula actuator 128 from the primed to the actuated configuration to cause movement of the cannula 102 relative to the stylet 104. This may be triggered using the stylet actuator 144. The stylet actuator 144 may be moved to engage with the locking mechanism 138 as described above to release the catch 140. This step is illustrated in FIGS. 5a and 5b. Once the locking mechanism 138 is released, the cannula actuator moves from the primed to the actuated configuration to move the cannula 102 into a position in which it at least partly surrounds the tissue sampling portion 120. In doing so, the tissue 121 in the tissue sampling portion 120 is cut from the surrounding tissue so that a sample is taken. The biopsy device 100 is then in the configuration shown in FIGS. 6a and 6b.

Figure 7A:
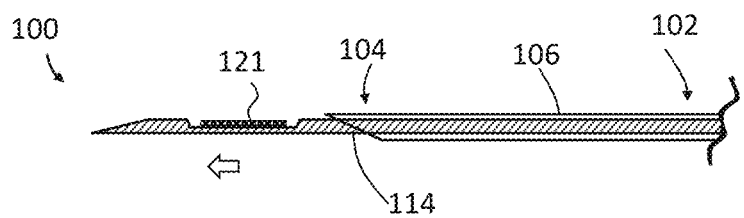
Figure 7B:
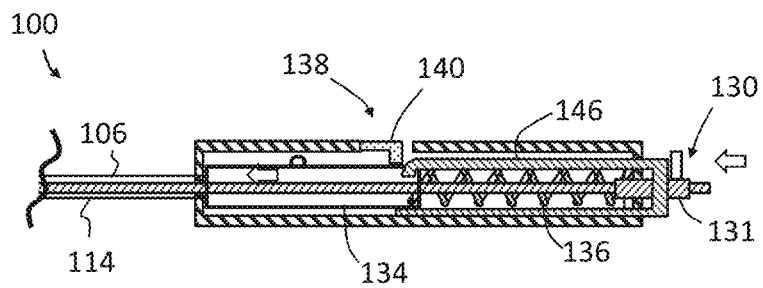

In a final step of the method, the selective coupling mechanism 130 may be used to decouple the stylet 104 from the actuator assembly 126. The stylet coupler 131 may be moved from the coupled to the uncoupled configuration so that the stylet 104 can be moved independently of the actuator assembly 126. The stylet 104 can therefore be moved in a distal direction to once again expose the tissue sampling portion 120 as shown in FIGS. 7a and 7b. Alternatively, the stylet 104 may be moved in a proximal direction so that it can be removed completely from the cannula lumen. The tissue 121 can then be conveniently recovered from the tissue sampling portion 120 without having to move the cannula actuator to the primed configuration (i.e. without returning to the configuration shown in FIGS. 4a and 4b).

The stylet coupler 131 may take a number of different forms to allow a selective coupling between the actuator assembly 126 and the stylet 104. The stylet coupler 131 may comprise a two part releasable coupling mechanism in which a first part is provided on part of the actuator assembly (e.g. on the stylet actuator 144 or the housing 132) with a second part provided on the stylet 104.

In some embodiments, a rotation of at least part of the stylet coupler 131 may cause movement between the stylet coupled configuration and the stylet uncoupled configuration. In other embodiments, the stylet coupler 131 may have other forms such that other types of relative movement facilities movement between the coupled and uncoupled configurations.

One embodiment of the stylet coupler 131 is illustrated in FIGS. 8a, to 10b. FIGS. 8a, 9a, and 10a show a distal end of the biopsy device 100 in three different positions during use. FIGS. 8b, 9b and 10b show corresponding proximal ends of the biopsy device 100.

In the embodiment shown in FIGS. 8b-10b, the stylet coupler 131 comprises a release wheel 148 coupled to the stylet 104. The stylet coupler 131 comprises a slotted member 150 that is arranged to engage with an engagement member 152 provided on the release wheel 148. The release wheel 148 and the slotted member 150 form a two-part coupling mechanism that allows the stylet 104 and actuator assembly 126 to be releasably coupled. The slotted member 150 is adapted to receive the engagement member 152 when they are aligned to allow relative movement between the stylet 104 and the stylet actuator 144 to which the slotted member 150 is coupled. In other embodiments, the release wheel 148 may be coupled to another part of the actuator assembly 126. In the stylet uncoupled configuration, the engagement member 152 is aligned with a slot 150a of the slotted member 150 such that the stylet 104 can move freely relative to the slotted member 150 (as shown in FIG. 10b). The stylet 104 can therefore be moved distally relative to the slotted member 150 (as shown by the arrow in FIG. 10b) such that the tissue sampling portion 120 of the stylet 104 is exposed, and the tissue 121 can be accessed. In the stylet coupled configuration, the release wheel 148 is rotated (as shown in FIG. 9a) relative to the slotted member 150 such that the engagement member 152 is misaligned with the slot 150a. The engagement member 152 then abuts the slotted member 150 and the actuator assembly 126 is operably coupled to the stylet 104 (as shown in FIG. 8a) via the stylet coupler 131.

Another embodiment of the stylet coupler 131 is shown in FIGS. 11b to 13b in different positions during use. FIGS. 11a, 12a and 13a show a distal end of the biopsy device 100. FIGS. 11b, 12b and 13b show a corresponding proximal end of the biopsy device 100. In this embodiment, the stylet coupler 131 comprises a luer lock coupling forming the two-part releasable coupling mechanism between the actuator assembly 126 and the stylet 104. In this embodiment, the stylet coupler comprises a luer lock connector 154b provided on the actuator assembly 126 in communication with the lumen of the cannula 102 and a corresponding luer lock connector 154a provided on the stylet 104.

The stylet 104 can be removed from the cannula lumen when the stylet coupler 131 is in the uncoupled configuration as shown in FIG. 13b. The luer lock connector 154b provided on the actuator assembly 126 is adapted to provide a connection to another device, e.g. a suction/aspiration device such as a syringe, once the stylet 104 has been removed.

In other embodiments, the stylet coupler 131 may have another form that may allow a rotational movement of part of the stylet coupler 131 to facilitate movement between the coupled and uncoupled configurations. In yet other embodiments, the stylet coupler 131 may be in a different form so that a movement other than rotation is required to facilitate movement between the coupled and uncoupled configurations. For example, another two-part coupling mechanism may be provided, such as a retaining clip that locks the stylet 104 and actuator together (e.g. a circlip).

Figure 14:
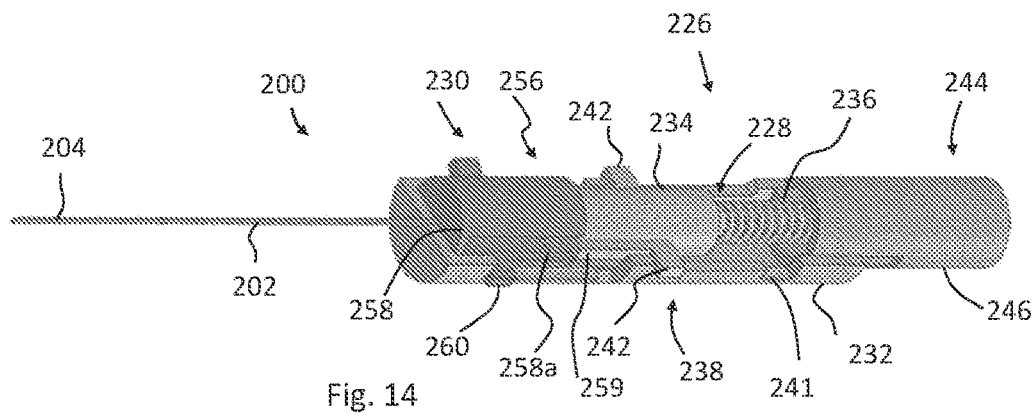
FIG. 14 shows a sectional schematic view of a biopsy device according to another embodiment.

Another embodiment of a biopsy device 200 is illustrated in FIG. 14. The biopsy device 200 shown in FIG. 14 has similar features to those of the biopsy device 100 described above. Corresponding reference numbers have been used for corresponding features. Anything described in connection with the biopsy device 100 may apply equally to the biopsy device of FIG. 14, and vice versa. The length of the stylet 204 and the cannula 202 shown in FIGS. 15 to 22 has been shortened for illustrative purposes.

Figure 15:
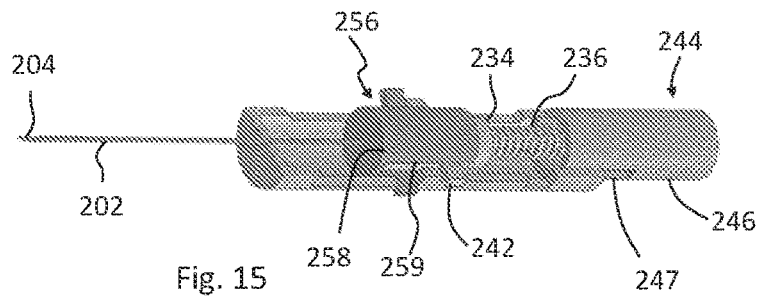
FIGS. 15 to 22 show an operation sequence of the biopsy device of FIG. 14.

The biopsy device 200 comprises the cannula 202 and the stylet 204 as illustrated in FIG. 15. The biopsy device 200 further comprises an actuator assembly 226 that is arranged to move the cannula between a retracted position and an extended position as described above. The actuator assembly also comprises a cannula actuator 228 that is movable between a primed and actuated configuration. The cannula actuator 228 similarly comprises a biasing member 236 in the form of a coiled spring and a locking mechanism 238 arranged to lock the cannula actuator 228 in the primed configuration. The cannula actuator 228 comprises a carriage or sliding member 234 arranged to slide within a housing 232 of the actuator assembly 226. The biasing member 236 is coupled between the sliding member 234 and the housing 232 in a similar manner to the embodiment shown in FIGS. 2a, 2b and 2c so as to provide relative movement between the cannula 202 and the housing 232 (and therefore between the cannula 202 and the stylet 204). In this embodiment, the locking mechanism 238 takes the form of a pair of protrusions 242 provided on the sliding member 234 that are each arranged to engage with one of a corresponding pair of slots 241 formed in the housing 232 to lock the sliding member in the primed configuration of the cannula actuator 228 against the action of the biasing member 236. Rotation of the sliding member 234 causes disengagement of the slots 241 and protrusions 242 to release the locking mechanism 238. Alternatively the mechanism may be constructed of one, three, four or more sets of protrusions 242 and corresponding slots 241. Other forms of locking mechanism are also possible.

A stylet actuator 244 is provided to allow actuation of the stylet. The stylet actuator 244 is configured to allow sliding movement of the stylet 204 relative to the housing 232 (and so relative to the cannula 202). The stylet actuator 244 comprises a sliding member 246 similarly to that of the embodiment of FIGS. 2a, 2b and 2c. In this embodiment however, the stylet actuator 244 does not provide any control of the cannula actuator 228.

The biopsy device 200 differs from the embodiment shown in FIGS. 2a, 2b and 2c in that the selective coupling mechanism 230 comprises a cannula coupler 256 rather than a stylet coupler 131. The cannula coupler 256 is movable between a cannula coupled configuration in which the cannula 202 is operably coupled to the actuator assembly 226, and a cannula uncoupled configuration in which the cannula is operably uncoupled from the actuator assembly 226. In the cannula coupled configuration, the cannula 202 is coupled to the cannula actuator 228 such that movement between the primed and actuated configurations causes movement of the cannula 202. In the cannula uncoupled configuration, the cannula 202 can be moved freely relative to cannula actuator 228 (and therefore freely relative to a handle portion and the stylet 104). Movement between the primed and actuated configurations causes no movement of the cannula 202. This allows the position of the cannula 202 to be adjusted without any associated use of the cannula actuator 228. For example, the position of the distal end of the cannula 202 can be repositioned (with the cannula actuator 228 in the primed configuration) relative to an outer sheath (e.g. labeled 102b in FIG. 11a). This may allow the distal end of the cannula 202 to be repositioned relative to the outer sheath without using up any of the travel of the cannula actuator 228 and ensure the cannula 202 is correctly positioned to avoid damage to a device working channel down which the biopsy device 200 is inserted.

Similarly to the stylet coupler 131, the cannula coupler 256 may take a number of different forms to allow a selective coupling between the actuator assembly 226 and the cannula 202. The cannula coupler 256 may comprise a two part releasable coupling mechanism in which a first part is provided on part of the actuator assembly 226 with a second part provided on cannula 202.

In the embodiment shown in FIG. 14, the cannula coupler 256 comprises a slotted member 258 coupled to the cannula 202 and a corresponding engagement member 258a coupled to the cannula actuator 228. In the described embodiment, the engagement member 258a is formed by part of the protrusions 242 that forms part of the locking mechanism 238. In other embodiments, a separate engagement member may be provided on part of the cannula actuator 228 to provide engagement with the slotted member 258.

In the cannula uncoupled configuration, the engagement member 258a is aligned with a slot 259 of the slotted member 258 such that the cannula 202 can move freely relative to the actuator. In the cannula coupled configuration, the slotted member 258 of the cannula coupler 256 is rotated relative to its orientation in the cannula coupled configuration such that the engagement member 258a is misaligned with the slot 259. In the coupled configuration, the engagement member 258a is therefore configured to engage the slotted member 258 so that movement of the cannula actuator 228 causes an associated movement of the cannula 202.

A rotation of at least part of the cannula coupler 256 therefore causes movement of the cannula coupler 256 between the cannula coupled configuration and the cannula uncoupled configuration. The embodiment shown in FIG. 14 is however only one example. In other embodiments, the slotted member 258 and the engagement member 258a may be reversed. In yet other embodiments, other two-part releasable coupling mechanisms may be provided to form the cannula coupler.

A locking mechanism 260 may be provided to lock the cannula coupler in the coupled or uncoupled configurations. The locking mechanism 260 may take the form of co-operating slots and protrusions in the slotted member 258 and the housing 232 as shown in the Figures. Other locking mechanisms may however be used.

Use of the biopsy device 200 shown in FIG. 14 to collect a tissue sample is shown in the sequence of FIGS. 15 to 22. FIG. 15 shows a starting position in which the cannula coupler 256 is in the uncoupled configuration. The protrusions 242 on the sliding member 234 is aligned with the slot 259 of the slotted member 258 so that movement of the sliding member 234 (e.g. actuated by the cannula actuator 228) does not result in any movement of the slotted member 258 and the cannula 202.

Figure 16:
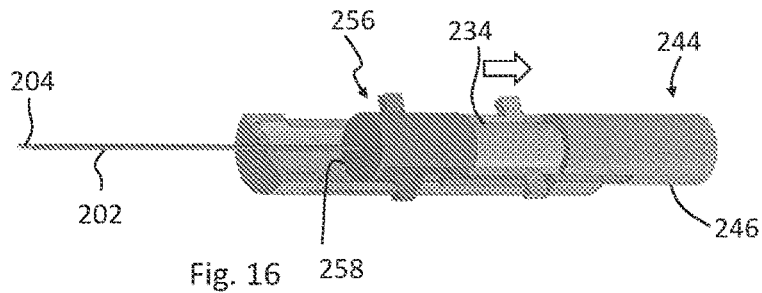

FIG. 16 shows movement of the cannula actuator 228 from the actuated to the primed configuration. This is achieved by movement of the sliding member 234 relative to the housing 232 to store energy in the biasing member 236.

Figure 17:
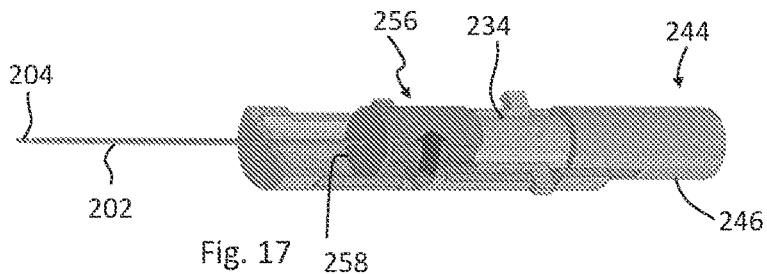

FIG. 17 shows movement of the cannula coupler 256 from the uncoupled to the coupled configuration. Rotation of the slotted member 258 relative to the sliding member 234 as shown by the arrow in FIG. 17 provides movement from the uncoupled to the coupled configuration by alignment of the protrusions 242 of the sliding member 234 and the slot 259 of the slotted member 258.

Figure 18:
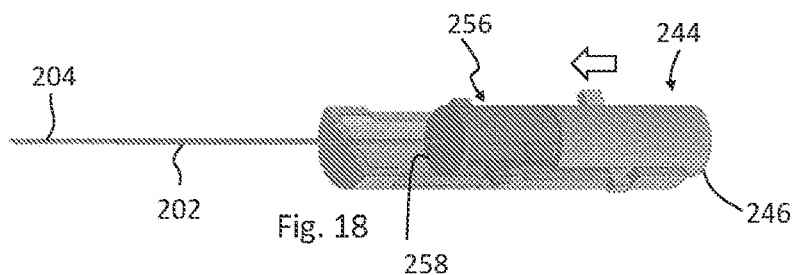

FIG. 18 shows the stylet 204 being advanced into the lesion in order to collect tissue into the tissue sampling portion. The stylet 204 is moved by movement of the stylet sliding member 246 of the stylet actuator 244 relative to the housing 232 (and the cannula 202) to extend the distal end of the stylet 204 out of the distal end of the cannula 202. As can be seen in FIG. 14, the sliding member 246 may comprise one or more slots 247 that may receive the protrusions 242 of the cannula actuator so that movement of the stylet actuator 244 does not affect the cannula actuator 228.

Figure 19:
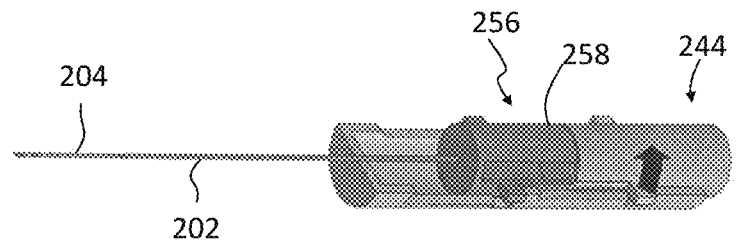

FIG. 19 shows release of the locking mechanism 238 by disengagement of the protrusions 242 and the corresponding slots 241 in the housing 232. This is achieved by a rotation of the sliding member 234 as shown by the arrow in FIG. 19. The stylet actuator 244 may be used to activate the cannula actuator 228 by moving the sliding member 234 of the cannula actuator 228 to the unlocked position.

Figure 20:
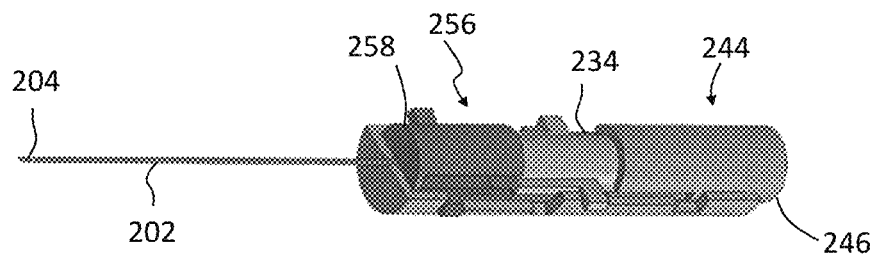

FIG. 20 shows movement of the cannula actuator 228 from the primed to the actuated configuration. Once the locking mechanism is released, the sliding member 234 is moved in a distal direction by the action of the biasing member 236. As the cannula coupler 256 is in the coupled configuration, a corresponding distal movement of the cannula 202 is produced. The cannula 202 is moved relative to the stylet 204 so that the tissue sampling portion is surrounded by the cannula and the tissue sample is cut away from surrounding tissue.

Figure 21:
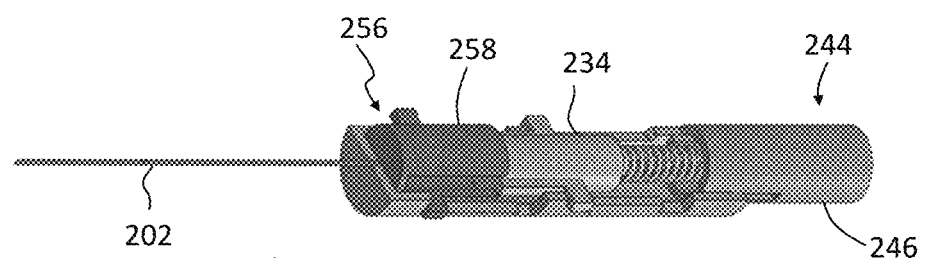
Figure 22:
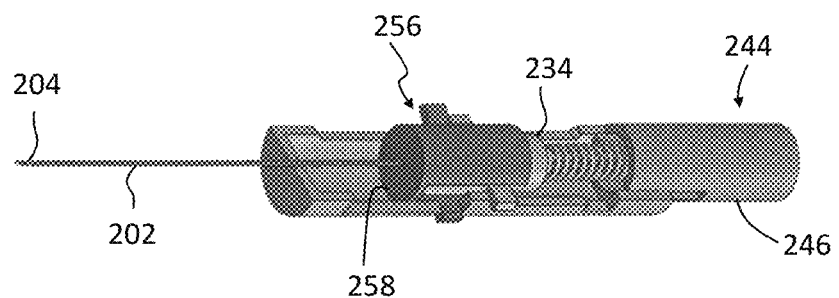

FIG. 21 shows the retraction of the stylet by moving the sliding member 246 of the stylet actuator 244 in a proximal direction. FIG. 22 then shows the cannula coupler 256 returned to the coupled configuration so as to return to the starting configuration.

In the embodiments described above the selective coupling mechanism either 130 or 230 comprises either the stylet coupler 131 or the cannula coupler 256. In yet other embodiments, the selective coupling mechanism either 130 or 230 can be provided with both theft cannula coupler 256 and the stylet coupler 131. For example, the embodiment shown in FIG. 14 can be modified such that the stylet coupler 131 is provided to releasably couple the stylet 204 and the stylet actuator 244.

The invention claimed is:

1. A biopsy device, comprising:
 a cannula comprising an elongate cannula body extending between a cannula distal end and a cannula proximal end to define a lumen, wherein the cannula comprises a cutting portion at the cannula distal end;
 a stylet comprising an elongate body having a stylet distal end and a stylet proximal end, the stylet being slidably disposed within the lumen, wherein the stylet comprises a tissue sampling portion, the tissue sampling portion being formed by a notch in the body of the stylet at or near the stylet distal end;
 an actuator assembly, the actuator assembly arranged to move the cannula relative to the stylet between a retracted position in which at least part of the tissue sampling portion is exposed and an extended position in which the cannula at least partly surrounds the tissue sampling portion, the actuator assembly comprising a cannula actuator moveable between a primed configuration and an actuated configuration to move the cannula between the retracted position and the extended position; and
 a selective coupling mechanism arranged to provide a selective coupling between the actuator assembly and the cannula, wherein:
 the selective coupling mechanism comprises a cannula coupler, the cannula coupler being movable between a cannula coupled configuration in which the cannula is coupled to the actuator assembly such that movement between the primed configuration and the actuated configuration of the cannula actuator causes movement of the cannula; and a cannula uncoupled configuration in which the cannula is uncoupled from the actuator assembly and can be moved freely relative to the cannula actuator; and a rotation of at least part of the cannula coupler causes movement of the cannula coupler between the cannula coupled configuration and the cannula uncoupled configuration;

one of the cannula actuator and the cannula coupler comprises a slotted member and the other of the cannula actuator and cannula coupler comprises a corresponding engagement member, wherein:

in the cannula uncoupled configuration, the engagement member is aligned with a slot of the slotted member such that the cannula can move freely relative to the actuator; and in the cannula coupled configuration, the cannula coupler is rotated such that the engagement member is misaligned with the slot whereby the engaging member engages the slotted member and movement of the cannula actuator causes movement of the cannula.

2. A biopsy device according to claim 1, wherein the selective coupling mechanism further comprises a stylet coupler, the stylet coupler being movable between:

a stylet coupled configuration in which the stylet is coupled to the actuator assembly; and a stylet uncoupled configuration in which the stylet is uncoupled from the actuator assembly.

3. A biopsy device according to claim 2, wherein the actuator assembly comprises a stylet actuator configured to actuate movement of the stylet relative to the cannula, wherein the stylet actuator is further configured to control or cause movement of the cannula actuator between the actuated configuration and the primed configuration.

4. A biopsy device according to claim 3, wherein the stylet actuator and the cannula actuator are operably coupled in the stylet coupled configuration such that, operation of the stylet actuator to cause movement of the stylet in a distal direction relative to the cannula activates movement of the cannula actuator from the primed configuration to the actuated configuration, and optionally wherein the actuator assembly comprises a locking mechanism arranged to releasably lock the cannula actuator in the primed configuration, and wherein the locking mechanism is releasable by the stylet actuator.

5. A biopsy device according to claim 3, wherein the stylet actuator and the cannula actuator are operably coupled in the stylet coupled configuration such that operation of the stylet actuator to cause movement of the stylet relative to the cannula causes movement of the cannula actuator from the actuated configuration to the primed configuration.

6. A biopsy device according to claim 2, wherein in the stylet uncoupled configuration, the stylet is movable in a distal direction relative to the cannula to an extended position in which a portion of the stylet having the tissue sampling portion is extended past the distal end of the cannula.

7. A biopsy device according to claim 2, wherein in the stylet uncoupled configuration, the stylet is movable in a proximal direction relative to the cannula so that it can be removed from the lumen of the cannula.

8. A biopsy device according to claim 7, wherein the stylet coupler comprises a luer lock connector in communication with the lumen of the cannula and a corresponding luer lock connector provided on the stylet, wherein optionally the luer lock connector in communication with the cannula lumen may be adapted to provide a connection to another device having a corresponding luer lock connector when the stylet is removed from the lumen of the cannula.

9. A biopsy device according to claim 2, wherein a rotation of at least part of the stylet coupler causes movement of the stylet coupler between the stylet coupled configuration and the stylet uncoupled configuration.

10. A biopsy device according to claim 9, wherein the stylet coupler comprises a release wheel mounted to the stylet, the release wheel having a second engagement member, and a second slotted member coupled to the actuator assembly, the second slotted member adapted to receive the engagement member, wherein:

in the stylet uncoupled configuration, the engagement member is aligned with a slot of the second slotted member such that the stylet can move freely relative to the actuator assembly; and in the stylet coupled configuration, the release wheel is rotated such that the second engagement member is misaligned with the slot of the second slotted member, whereby the second engagement member abuts the second slotted member such that the actuator assembly is operably coupled to the stylet.

11. A biopsy device according to claim 1, wherein the cannula actuator comprises a biasing member formed from a resilient member and wherein in the primed configuration the cannula actuator is biased towards the actuated configuration, and wherein the resilient member is a coiled spring.

12. A method of collecting a tissue sample using the biopsy device of claim 1, the method comprising:

moving the cannula actuator from the actuated configuration to the primed configuration;

extending the stylet relative to the cannula to expose the tissue sampling portion and to receive tissue in the tissue sampling portion; and moving the cannula actuator from the primed configuration to the actuated configuration to cause movement of the cannula relative to the stylet, whereby tissue in the tissue sampling portion is cut from the surrounding tissue so that a tissue sample is taken, wherein the method further comprises using the selective coupling mechanism to decouple the cannula from the actuator assembly.

13. The method of claim 12, comprising:

using the selective coupling mechanism to decouple the stylet from the actuator assembly once the cannula actuator is moved to the actuated configuration and a tissue sample taken; and moving the stylet independently of the cannula actuator to recover the tissue sample.

14. The method of claim 13, wherein, once the selective coupling mechanism has been decoupled, moving the stylet in a distal direction to expose the tissue sampling portion and so a tissue sample can be recovered.

15. The method of claim 13, wherein, once the selective coupling mechanism has been decoupled, moving the stylet in a proximal direction so that it can be removed completely from the cannula lumen to recover the tissue sample.

* * * * *